United States Patent [19]

Rasberger

[11] 4,276,232
[45] Jun. 30, 1981

[54] PHOSPHORUS STABILIZERS

[75] Inventor: Michael Rasberger, Riehen, Switzerland

[73] Assignee: Ciba-Geigy Corporation, Ardsley, N.Y.

[21] Appl. No.: 82,499

[22] Filed: Oct. 9, 1979

Related U.S. Application Data

[63] Continuation of Ser. No. 922,392, Jul. 6, 1978, abandoned.

[30] Foreign Application Priority Data

Jul. 7, 1977 [CH] Switzerland ............ 8431/77

[51] Int. Cl.$^3$ .............................................. C07F 9/48
[52] U.S. Cl. .............................. 260/936; 260/45.8 R; 260/45.75 R; 260/927 R
[58] Field of Search ............... 260/45.75 R, 927 R, 260/936

[56] References Cited

U.S. PATENT DOCUMENTS 3,702,878  11/1972  Saito .......................... 260/45.8 R

FOREIGN PATENT DOCUMENTS 2034887  1/1972  Fed. Rep. of Germany.

Primary Examiner—V. P. Hoke
Attorney, Agent, or Firm—Harry Falber

[57] ABSTRACT

Alkylated 6-phenoxy-dibenz[c,e]-[1,2]oxaphosphorines are suitable as stabilizers for organic material.

1 Claim, No Drawings

PHOSPHORUS STABILIZERS

This is a continuation of application Ser. No. 922,392 filed on July 6, 1978, now abandoned.

The invention relates to new phosphonites, to the manufacture thereof, to their use as stabilisers for plastics and elastomers, and also to the polymers stabilised with these phosphonites.

Phosphonites are known stabilisers, especially 6-phenoxydibenz[c,e]-[1,2]-oxaphosphorine and 6-(2,6-di-tert.-butyl-4-methyl-phenoxy)-dibenz[c,e]-[1,2]-oxaphosphorine (Examples 9 and 10 of German Offenlegungsschrift No. 2,034,887). However, these phosphonites do not in every respect meet the high requirements which should be met by a stabiliser, particularly in respect of storage stability, absorption of water, sensitivity to hydrolysis, processing stabilisation, colour improvement, volatility, compatibility and improved stability to light.

It was the object of this invention therefore to provide stabilisers which do not have the disadvantages mentioned or have them to a lesser extent.

Accordingly, the invention relates to phosphonites of the formulae I and II

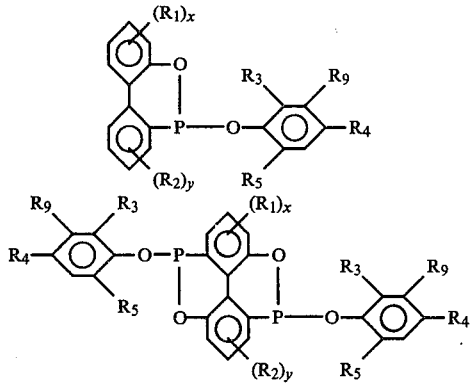

wherein
- $R_1$ and $R_2$ independently of one another are a substituted or unsubstituted hydrocarbon radical, or halogen,
- x and y independently of one another are 0, 1, 2 or 3,
- $R_3$ and $R_5$ independently of one another are hydrogen or a substituted or unsubstituted hydrocarbon radical,
- $R_4$ is hydrogen, a substituted or unsubstituted hydrocarbon radical, $-CO-X-R_6$, $-PO-(OR_8)_2$ or $-OR_8$, wherein X is $-O-$ or $-NR_7-$, $R_6$ and $R_7$ independently of one another are hydrogen or a substituted or unsubstituted hydrocarbon radical, and $R_8$ is a substituted or unsubstituted hydrocarbon radical, the condition being that not all three radicals $R_3$, $R_4$ and $R_5$ are simultaneously hydrogen, and that, if $R_3$ and $R_5$ are tert.-butyl, $R_4$ is not methyl, and $R_9$ is hydrogen and, if $R_3$ is hydrogen, also methyl.

A substituted or unsubstituted hydrocarbon radical $R_1$ or $R_2$ is especially a radical of this type having 1-8 C atoms, such as straight-chain or branched-chain alkyl having 1-8 C atoms, for example methyl, i-propyl or tert.-butyl, and halogen $R_1$ or $R_2$ is particularly chlorine.

A substituted or unsubstituted hydrocarbon radical $R_3$ or $R_5$ is especially a radical of this type having 1-25 C atoms, such as $C_1$-$C_{12}$ alkyl, in particular $C_1$-$C_8$ alkyl, for example methyl, ethyl, i-propyl, tert.-butyl, tert.-pentyl or tert.-octyl, $C_3$-$C_4$ alkenyl, for example allyl or methallyl, $C_3$-$C_4$ alkynyl, for example propargyl, $C_5$-$C_{12}$ cycloalkyl, for example cyclohexyl, ($C_1$-$C_8$ alkyl)-$C_5$-$C_8$ cycloalkyl, for example α-methylcyclohexyl, $C_7$-$C_{14}$ aralkyl, for example benzyl, α-methylbenzyl or α,α-dimethylbenzyl, $C_6$-$C_{14}$ aryl, for example phenyl, or $C_7$-$C_{14}$ alkaryl, such as ($C_1$-$C_8$ alkyl)-phenyl, for example tolyl. $R_3$ and $R_5$ can also be substituted alkyl, especially having a total of 1-25 C atoms, such as ($C_1$-$C_8$ alkyl)—CO—X—$R_6$, in which X and $R_6$ have the meaning defined above and that defined below as being preferred, such as 1,1-dimethyl-4-ethoxycarbonyl-butyl, or di-($C_1$-$C_8$ alkyl)-phosphonomethyl, for example diethylphosphonomethyl, or $C_1$-$C_{36}$ aminoalkyl, especially aminomethyl, such as ($C_1$-$C_{18}$ alkyl)-aminomethyl or di-($C_1$-$C_{18}$ alkyl)-aminomethyl, for example dimethylaminomethyl or di-n-butylaminomethyl, or ($C_1$-$C_{18}$ acyloxy)-methyl or ($C_1$-$C_{18}$ acylthio)-methyl, such as ($C_1$-$C_{18}$ alkanoyloxy)-methyl or ($C_1$-$C_{18}$ alkanoylthio)-methyl, N-alkylated ($C_1$-$C_{18}$ carbamoyloxy)-methyl, N-alkylated ($C_1$-$C_{18}$ carbamoylthio)-methyl or N-alkylated ($C_1$-$C_{18}$ thiocarbamoylthio)methyl, for example acetoxymethyl, propionylthiomethyl, N,N-di-n-butyl-carbamoyloxymethyl, N,N-di-n-butyl-carbamoylthiomethyl, N,N-di-n-butyl-thiocarbamoylthio-methyl or N,N-di-n-octyl-thiocarbamoylthiomethyl. Moreover, $R_5$ can also be: $C_1$-$C_{18}$ alkoxycarbonylmethyl, for example methoxycarbonylmethyl or n-octadecyloxycarbonylmethyl, or 2-($C_1$-$C_{18}$ alkoxycarbonyl)ethyl, such as 2-(methoxycarbonyl)-ethyl, or cyanomethyl.

As a substituted or unsubstituted hydrocarbon radical, $R_4$ has in particular the meanings defined in general and as being preferred for $R_3$/$R_5$, and as —CO—X—$R_6$, $R_4$ is in particular ($C_1$-$C_{18}$ alkoxy)-carbonyl, for example methoxycarbonyl or n-octadecyloxycarbonyl, ($C_6$-$C_{14}$ aryloxy)-carbonyl, such as phenoxycarbonyl, or ($C_1$-$C_{18}$ alkyl)-phenoxycarbonyl, for example 2,4-di-tert.-butyl-phenoxycarbonyl, or ($C_5$-$C_7$ cycloalkoxy)-carbonyl, for example cyclohexyloxycarbonyl. As $-PO-(OR_8)_2$, $R_4$ is especially $-PO-(OR_8)_2$ in which $R_8$ is $C_1$-$C_{18}$ alkyl, such as diethylphosphono, di-n-butylphosphono or di-n-octylphosphono.

As $-OR_8$, $R_4$ is in particular $C_1$-$C_{18}$ alkoxy, for example methoxy.

$R_7$ is in particular hydrogen or $C_1$-$C_{18}$ alkyl, for example methyl.

$R_9$ is in particular hydrogen.

Preferred phosphonites of the formula I are those wherein
- $R_1$ is $C_1$-$C_8$ alkyl,
- x is 0, 1 or 2,
- y is 0,
- $R_3$ and $R_5$ independently of one another are hydrogen, substituted or unsubstituted $C_1$-$C_{25}$ alkyl, $C_3$-$C_4$ alkenyl, $C_3$-$C_4$ alkynyl, $C_5$-$C_{12}$ cycloalkyl, $C_6$-$C_{13}$ α-methylcycloalkyl, $C_7$-$C_{14}$ aralkyl, $C_7$-$C_{14}$ alkaryl or $C_6$-$C_{14}$ aryl,
- $R_4$ has one of the meanings defined for $R_3$/$R_5$ or is ($C_1$-$C_{18}$ alkoxy)-carbonyl, ($C_5$-$C_7$ cycloalkoxy)-carbonyl, phenoxycarbonyl, ($C_1$-$C_{12}$ alkyl)-phenoxycarbonyl, $C_1$-$C_{18}$ alkoxy or 2-($C_1$-$C_{18}$ alkoxycarbonyl)-ethyl, the condition being that not all three radicals $R_3$, $R_4$ and $R_5$ are simultaneously hydrogen, and that, if $R_3$ and $R_5$ are tert.-butyl, $R_4$ is not methyl, and $R_9$ is hydrogen.

Particularly preferred phosphonites of the formula I are those wherein x and y are 0, $R_3$ and $R_5$ independently of one another are hydrogen, $C_1$–$C_{12}$ alkyl, cyclohexyl, α-methylcyclohexyl, benzyl, α,α-dimethylbenzyl, phenyl or ($C_1$–$C_{18}$ alkoxy)-carbonyl-$C_1$–$C_8$ alkyl, $R_4$ has one of the meanings defined for $R_3$/$R_5$, or is ($C_1$–$C_{18}$ alkoxy)-carbonyl, or 2-($C_1$–$C_{18}$ alkoxycarbonyl)-ethyl, the condition being that not all three radicals $R_3$, $R_4$ and $R_5$ are simultaneously hydrogen, and that, if $R_3$ and $R_5$ are tert.-butyl, $R_4$ is not methyl, and $R_9$ is hydrogen.

The invention relates above all to phosphonites of the formula I wherein x and y are 0, $R_3$ and $R_5$ independently of one another are $C_1$–$C_{12}$ alkyl, cyclohexyl, α-methylcyclohexyl, benzyl, α,α-dimethylbenzyl or phenyl, or one of $R_3$ and $R_5$ is hydrogen and the other has the above meaning, $R_4$ is hydrogen, $C_1$–$C_{12}$ alkyl, ($C_1$–$C_{18}$ alkoxy)-carbonyl or 2-($C_1$–$C_{18}$ alkoxycarbonyl)-ethyl, the condition being that, if $R_3$ and $R_5$ are tert.-butyl, $R_4$ is not methyl, and R is hydrogen.

In addition to the compounds named in the Examples, preferred compounds are in particular the following:

1. 6-(2,6-di-ethyl-phenoxy)-dibenz[c,e]-[1,2]oxaphosphorine,
2. 6-(2,4,6-tri-methyl-phenoxy)-dibenz[c,e]-[1,2]oxaphosphorine,
3. 6-(2-phenyl-phenoxy)-dibenz[c,e]-[1,2]oxaphosphorine,
4. 6-(2,6-di-isopropyl-phenoxy)-dibenz[c,e]-[1,2]oxaphosphorine.
5. 6-(2,6-di-phenyl-4-methoxy-phenoxy)-dibenz[c,e]-[1,2]-oxaphosphorine,
6. 6-(2,6-di-tert.-butyl-4-n-octadecyloxycarbonyl-phenoxy)-dibenz[c,e]-[1,2]oxaphosphorine,
7. 6-[2,6-di-tert.-butyl-4-diethylphosphono-phenoxy)-di-benz[c,e]-[1,2]oxaphosphorine,
8. 6-(2-methyl-4-di-n-butylaminomethyl-6-tert.-butyl-phenoxy)-dibenz[c,e]-[1,2]oxaphosphorine,
9. 6-[2,6-di-tert.-butyl-4-(N,N-di-n-octylthiocarbamoyl-thiomethyl)-phenoxy]-dibenz[c,e]-[1,2]oxaphosphorine,
10. 6-[2,6-(di-1,1-dimethyl-4-ethoxycarbonyl-butyl)-4-methyl-phenoxy]-dibenz[c,e]-[1,2]oxaphosphorine,
11. 6-(2-methyl-4-n-octadecyloxycarbonylmethyl-6-tert.-butyl-phenoxy)-dibenz[c,e]-[1,2]oxaphosphorine,
12. 6-(2,6-di-i-propyl-4-(2-methoxycarbonyl-ethyl)-phenoxyl-dibenz[c,e]-[1,2]oxaphosphorine,
13. 6-[2-methyl-4-(2,4-di-tert.-butyl-phenoxycarbonyl)-6-tert.-butyl-phenoxy[-dibenz[c,e]-[1,2]oxaphosphorine,
14. 6-(2-cyclohexyl-4-tert.-octyl-phenoxy)-dibenz[c,e]-[1,2]-oxaphosphorine,
15. 6-(2-methyl-4-diethylphosphonomethyl-6-α,α-dimethyl-benzyl-phenoxy)-dibenz[c,e]-[1,2]oxaphosphorine,
16. 6-(2,4-di-i-propyl-6-phenyl-phenoxy)-dibenz[c,e]-[1,2]-oxaphosphorine,
17. 2-tert.-butyl-6-(2,4-di-tert.-butyl-phenoxy)-dibenz[-c,e]-[1,2]oxaphosphorine,
18. 2,4-di-tert.-butyl-6-(2,4-di-tert.-butyl-phenoxy)-dibenz[c,e]-[1,2]oxaphosphorine,
19. 2,4-di-tert.-butyl-6-(2,6-di-i-propyl-4-tert.-octyl-phenoxy)-dibenz[c,e]-[1,2]oxaphosphorine,
20. 4-tert.-butyl-6-(2,4-di-tert.-butyl-6-phenyl-phenoxy)-dibenz[c,e]-[1,2]oxaphosphorine,
21. 2,4-di-tert.-butyl-6-[2-methyl-4-(2-n-octadecyloxy-carbonylethyl)-6-tert.-butylphenoxy]-dibenz[c,e]-[1,2]-oxaphosphorine,
22. 2,4-di-tert.-butyl-6-(2,6-di-tert.-butyl-4-methyl-phenoxy)-dibenz[c,e]-[1,2]oxaphosphorine,
23. 2,4-di-tert.-butyl-6-(2,6-di-tert.-butyl-phenoxy)-dibenz[c,e]-[1,2]oxaphosphorine,
24. 6-(2,6-di-tert.-butyl-4-diethylphosphonomethyl-phenoxy)-dibenz[c,e]-[1,2]oxaphosphorine,
25. 6-(2,6-di-tert.-butyl-4-tert.-octyl-phenoxy)-dibenz-[c,e]-[1,2]oxaphosphorine,
26. 6-(2-tert.-butyl-4-methyl-6-α-methylcyclohexyl-phenoxy)-dibenz[c,e]-[1,2]oxaphosphorine,
27. 6-[2,6-di-(α,α-dimethylbenzyl)-4-n-octadecyloxycarbonyl-methyl-phenoxy]-dibenz[c,e]-[1,2]oxaphosphorine,
28. 6-(2-tert.-butyl-4-methyl-6-tert.-pentyl-phenoxy)-dibenz[c,e]-[1,2]oxaphosphorine,
29. 6-(2-tert.-butyl-4,6-di-tert.-octyl-phenoxy)-dibenz-[c,e]-[1,2]oxaphosphorine,
30. 6-[2,6-di-tert.-butyl-4-(2,4-di-tert.-butyl-phenoxy-carbonyl)-phenoxy]-dibenz[c,e]-[1,2]oxaphosphorine,
31. 6-[2,6-di-tert.-pentyl-4-(2-ethoxycarbonyl-ethyl)-phenoxy]-dibenz[c,e]-[1,2]oxaphosphorine,
32. 6-[2-tert.-butyl-4-methyl-6-(1,1-dimethyl-4-ethoxy-carbonyl-butyl)-phenoxy]-dibenz[c,e]-[1,2]oxaphosphorine,
33. 6-(2,6-di-tert.-butyl-4-cyanomethyl-phenoxy)-dibenz-[c,e]-[1,2]oxaphosphorine,
34. 6-tert.-butyl-5-methyl-phenoxy)-dibenz[c,e]-[1,2]-oxaphosphorine, and
35. 6-(2,4-di-tert.-butyl-5-methyl-phenoxy)-dibenz[c,e]-[1,2]-oxaphosphorine.

The phosphonites of the formulae I and II can be produced by methods known per se, especially by esterification or transesterification reactions, for example by reacting a phosphonite of the formulae

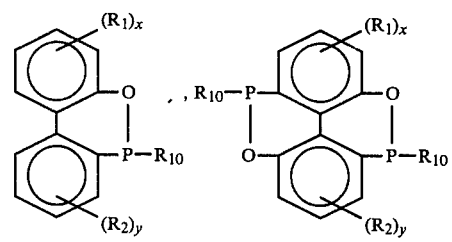

wherein $R_{10}$ is a reactive group, and $R_1$, $R_2$, x and y have the meanings defined in the foregoing, with a phenol of the formula

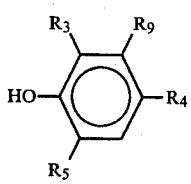

wherein $R_3$, $R_4$, $R_5$ and $R_9$ have the meanings defined above.

A reactive group $R_{10}$ is for example halogen, especially chlorine; alkoxy or substituted or unsubstituted phenoxy.

The reaction can be performed in a manner known per se, for example by heating, preferably to above about 80° C., in particular above 150° C., such as 150°–240° C., for example 220° C., in the course of which H $R_{10}$ is split off, wherein $R_{10}$ has the meaning defined above; or instead in the presence of bases, such as amines, for example triethylamine, pyridine, N,N-dimethylaniline or sodium carbonate, preferably in an inert solvent, such as aprotic solvents, for example ligroin, toluene, dimethylformamide, dimethylacetamide, sulpholane, methyl ethyl ketone, acetonitrile or ethyl acetate; and also amine bases in excess can be used and these can at the same time serve as solvents (see also German Offenlegungsschrift No. 2,034,887).

The starting materials are known and can, if they are novel, be produced by methods analogous to known methods. P-Cl phosphonites are known, for example, from German Offenlegungsschrift No. 2,034,887, whilst the starting phenols are compounds which have been known for a long time and which are in many cases available commercially.

The compounds of the formula I/II can be used according to the present invention as stabilisers for plastics and elastomers to protect these from damage caused by the action of oxygen, light and heat. Examples of plastics concerned are the polymers listed in the German Offenlegungsschrift No. 2,456,864 on pages 12–14.

Suitable substrates are, for example:

1. Polymers which are derived from mono-substituted hydrocarbons, such as polyolefins, for example low density and high density polyethylene, which can be crosslinked, polypropylene, polyisobutylene, polymethylbut-1-ene and polymethylpent-1-ene.
2. Mixtures of the homopolymers mentioned under 1, for example mixtures of polypropylene and polyethylene, of polypropylene and polybut-1-ene and of polypropylene and polyisobutylene.
3. Copolymers of the monomers on which the homopolymers mentioned under 1 are based, such as ethylene/propylene copolymers, propylene/but-1-ene copolymers, propylene/isobutylene copolymers and ethylene/but-1-ene copolymers, and also terpolymers of ethylene and propylene with a diene, for example hexadiene, di-cyclopentadiene or ethylidenenorbornene.
4. Polystyrene and its copolymers, such as SAN, ABS, IPS, ASA, and EP-modified styrene copolymers.
5. Polyamides.
6. Linear polyesters.
7. Polyurethanes.
8. Polycarbonates.
9. Elastomers, such as polybutadiene, SBR, polyisoprene, polychloroprene and nitrile rubber.
10. Thermoplastic elastomers, such as SBS, SIS and S-EP-S.
11. Polyvinyl chloride and the like.
12. Lubricating oils having a synthetic or mineral base.

The present invention relates also to a process for stabilising polymers against thermooxidative degradation during production, isolation, processing and use, which process comprises incorporating into the polymer at least one compound of the formula I/II.

The compounds of the formula I/II are incorporated into the substrates at a concentration of 0.005 to 5 percent by weight, calculated relative to the material to be stabilised.

Preferably 0.01 to 1.0 percent by weight, and particularly preferably 0.02 to 0.5 percent by weight, of the compounds, relative to the material to be stabilised, is incorporated into this material. Incorporation is effected for example by mixing at least one of the compounds of the formula I/II, and optionally further additives, by methods customary in the art, into the polymer either before or during shaping, or alternatively by application of the dissolved or dispersed compounds to the polymers, optionally with subsequent removal of the solvent by evaporation.

The new compounds can also be added in the form of a masterbatch, which contains these compounds for example at a concentration of 2.5 to 25 percent by weight, to the plastics to be stabilised.

In the case of crosslinked polyethylene, the compounds are added before crosslinking.

The invention relates therefore also to the plastics which are stabilised by the addition of 0.01 to 5 percent by weight of a compound of the formula I/II, and which can optionally contain further additives. The plastics stabilised in this way can be used in the widest variety of forms, for example as films, fibres, tapes or profiles, or as binders for lacquers, adhesives or putties.

Examples of further additives which can be used together with the stabilisers according to the invention are: antioxidants, UV absorbers and light stabilisers, such as 2-(2'-hydroxyphenyl)-benztriazoles, 2,4-bis-(2'-hydroxyphenyl)-6-alkyl-s-triazines, 2-hydroxybenzophenones, 1,3-bis-(2'-hydroxybenzoyl)-benzenes, esters of substituted or unsubstituted benzoic acids and acrylates, and also nickel compounds, sterically hindered amines, oxalic acid diamides, metal deactivators, phosphites, compounds which destroy peroxide, polyamide stabilisers, basic Co stabilisers, nucleating agents or other additives, for example plasticisers, lubricants, emulsifiers, fillers, carbon black, asbestos, kaolin, talc, glass fibres, pigments, optical brighteners, flameproofing agents and antistatic agents.

The invention is further illustrated by the following Examples.

EXAMPLES 1–18

10 g (0.0426 mol) of 6-chloro-dibenz[c,e]-[1,2]-oxaphosphorine, 10 g of 2,6-di-isopropyl-4-tert.-butylphenol and 30 ml of triethylamine are reacted for 15 hours at an internal temperature of 110° C.

After the reaction has ended, the reaction mixture is taken up in 100 ml of toluene, the solution is filtered, the filtrate is concentrated under reduced pressure and the residue is recrystallised from acetonitrile. The resulting 6-(2,6-di-isopropyl-4-tert.-butyl-phenoxy)-dibenz[c,e]-[1,2]oxaphosphorine melts at 128°–130° C. (compound 1).

The following compounds are obtained analogously:

2. 6-(2,6-di-tert.-butyl-phenoxy)-dibenz[c,e]-[1,2]oxaphosphorine, melting point 152° C.,
3. 6-(2,6-di-tert.-butyl-4-isopropyl-phenoxy)-dibenz[c,e]-[1,2]oxaphosphorine, melting point 95°–96° C.,
4. 6-[2,6-di-tert.-butyl-4-(2-methoxycarbonyl-ethyl)-phenoxy]-dibenz[c,e]-[1,2]oxaphosphorine, melting point 100° C.,
5. 6-[2,6-di-tert.-butyl-4-(2-n-octadecyloxycarbonylethyl)phenoxy]-dibenz[c,e]-[1,2]oxaphosphorine, melting point 75° C.,
6. 6-(2,4,6-tri-tert.-butyl-phenoxy)-dibenz[c,e]-[1,2]-oxaphosphorine, melting point 149° C.,
7. 6-(2,4,6-tri-isopropyl-phenoxy)-dibenz[c,e]-[1,2]oxaphosphorine, melting point 112° C.,
8. 6-(2,4-di-tert.-butyl-phenoxy)-dibenz[c,e]-[1,2]oxaphosphorine, melting point <50° C.,
9. 6-(2,4-di-tert.-butyl-6-methyl-phenoxy)-dibenz[c,e]-[1,2]oxaphosphorine, melting point 110° C.,
10. 6-(2-tert.-butyl-6-methyl-phenoxy)-dibenz[c,e]-[1,2]-oxaphosphorine, melting point 98°–100° C.,
11. 6-(2,4-di-tert.-octyl-phenoxy)-dibenz[c,e]-[1,2]oxaphosphorine, melting point 109° C.,
12. 6-{2,4-di-(α,α-dimethylbenzyl)-phenoxy}-dibenz[c,e]-[1,2]-oxaphosphorine, melting point 130° C.,
13. 6-(2,4-di-tert.-amyl-phenoxy)-dibenz[c,e]-[1,2]-oxaphosphorine, boiling point 180° C./0.05 mm Hg,
14. 6-(2-tert.-butyl-phenoxy)-dibenz[c,e]-[1,2]oxaphosphorine, boiling point 163° C./0.04 mm Hg,
15. 6-(2,6-di-tert.-butyl-4-methoxy-phenoxy)-dibenz[c,e]-[1,2]-oxaphosphorine, melting point 104°–105° C.,
16. 6-(1,1,3,3-tetramethyl-6-tert.-butyl-5-indanoxy)-dibenz[c,e]-[1,2]-oxaphosphorine, melting point 140° C.,
17. 6-(1,1,3,3-tetramethyl-6-tert.-octyl-5-indanoxy)-dibenz[c,e]-[1,2]oxaphosphorine, melting point 126° C., and
18. 6-(2,4-dimethyl-6-tert.-butylphenoxy)-dibenz[c,e]-[1,2]oxaphosphorine, melting point 126° C.

EXAMPLE 19

100 parts of polycarbonate granules (which have previously been dried for 12 hours at 120° C. in a vacuum oven) are mixed, in a shaking apparatus, with 0.1 part of the compound 11. The mixture obtained is extruded in a laboratory single-screw extruder at 280° C. nozzle temperature, and subsequently granulated. The granules without additive, which are required for the purpose of comparison, are produced in an analogous manner. Before further processing, the granules are dried for 12 hours in a vacuum oven at 120° C.

The test for effectiveness of the stabiliser in preventing yellowing of the material is carried out in a laboratory injection moulding machine at a maximum of 310° C. The yellowing of the 2 mm thick injection-moulded sheets is assessed by measurement of the Yellowness Index according to ASTM 1925-63. The values in the Table show that the sheets containing the stabiliser exhibit less yellowing both immediately after they are produced and after they have been oven-aged at 140° C. (higher Yellowness Index = more severe yellowing).

| Stabiliser | Yellowness Index | |
|---|---|---|
| | Immediately after being produced | After 100 days of oven-ageing at 140° C. |
| none | 9.3 | 48.3 |
| 0.1% of compound | 4.2 | 44.2 |
| No. 11 | | |

EXAMPLE 20

100 parts of polypropylene powder (Propathene HF 20, ICI) are mixed together with 0.1 part of calcium stearate, with compound 11 in the amounts given in the following Table, and with pentaerythritol-tetrakis-[3-(3,5-di-tert.-butyl-4-hydroxyphenyl)-propionate] (0.1 part in Table A and 0.05 part in Table B).

The resulting mixtures are extruded 5 times successively in a single screw extruder at a maximum of 260° C. in one series, and in another series 3 times successively in the same extruder but at 280° C., with a speed of 100 rpm in each case. The melt index of the polymer is measured after the 1st, 3rd and 5th extrusion and after the 1st and 3rd extrusion, respectively; and for this purpose the load is 2,160 g, the temperature 230° C. and the melt index is expressed in grams per 10 minutes. The degradation of the polymer is indicated by a rise in the melt index.

TABLE A

| Stabiliser | Melt index after several extrusions | | | | |
|---|---|---|---|---|---|
| | at 260° C. | | | at 280° C. | |
| | 1st | 3rd | 5th | 1st | 3rd |
| none | 6.3 | 8.9 | 15.0 | 7.1 | 21.4 |
| with 0.025 part of compound 11 | 3.0 | 3.8 | 5.1 | 3.4 | 5.1 |

TABLE B

| Stabiliser | Melt index after several extrusions | | | | |
|---|---|---|---|---|---|
| | at 260° C. | | | at 280° C. | |
| | 1st | 3rd | 5th | 1st | 3rd |
| none | 6.3 | 8.9 | 15.0 | 7.1 | 21.4 |
| 0.05 part of compound 2 | | | | 3.7 | 7.5 |
| 0.05 part of compound 6 | | | | 4.0 | 11.0 |
| 0.1 part of compound 8 | 2.4 | 3.0 | 4.1 | | |
| 0.05 part of compound 9 | | | | 3.4 | 5.2 |
| 0.025 part of compound 11 | 3.6 | 5.3 | 7.9 | 4.7 | 9.8 |
| 0.05 part of compound 11 | 2.6 | 3.3 | 4.2 | 3.2 | 4.6 |
| 0.1 part of compound 11 | 2.9 | 3.2 | 3.5 | 3.3 | 4.4 |
| 0.05 part of compound 13 | | | | 5.7 | 14.0 |

EXAMPLE 21

The procedure as described in Example 20 is followed except that a different polypropylene powder is used (Shell Carlona HY 61/1090/1324), and 0.07 part of pentaerythritoltetrakis-[3-(3,5-di-tert.-butyl-4-hydroxyphenyl)-propionate] is added.

| Stabiliser | Melt index after several extrusions | | | | |
|---|---|---|---|---|---|
| | at 260° C. | | | at 280° C. | |
| | 1st | 3rd | 5th | 1st | 3rd |
| none | 5.0 | 7.8 | 11.3 | 7.4 | 17.4 |

-continued

| Stabiliser | Melt index after several extrusions | | | | |
|---|---|---|---|---|---|
| | at 260° C. | | | at 280° C. | |
| | 1st | 3rd | 5th | 1st | 3rd |
| with 0.025 part of compound 11 | 2.3 | 3.4 | 5.2 | 3.0 | 5.5 |
| with 0.05 part of compound 11 | 2.0 | 2.3 | 3.0 | 2.2 | 3.5 |

EXAMPLE 22 (POLYETHYLENE)

100 parts of high-molecular weight polyethylene powder (Lupolen 52602, BASF) are mixed with 0.05 part of pentaerythritol-tetrakis-[3-(3,5-di-tert.-butyl-4-hydroxyphenyl)-propionate] and with one of the compounds according to the invention, as indicated in the Table below, and the mixture is kneaded in a Brabender plastograph at 220° C. at a speed of 50 revolutions per minute. During this time, the kneading resistance is continuously recorded as a turning moment. In the course of the kneading treatment, the polymer, after a prolonged period of remaining constant, commences to crosslink, a change which can be ascertained by the rapid increase in the turning moment. The effectiveness of the stabilisers is manifested by a lengthening of the time in which conditions remain constant

| Stabiliser | Time in minutes until the turning moment changes |
|---|---|
| 0.1 part of compound 1 | 7 |
| 0.1 part of compound 2 | 7 |
| 0.1 part of compound 3 | 11 |
| 0.1 part of compound 4 | 10 |
| 0.1 part of compound 5 | 5 |
| 0.1 part of compound 6 | 8 |
| 0.1 part of compound 7 | 6 |
| 0.1 part of compound 8 | 17 |
| 0.1 part of compound 9 | 13 |
| 0.1 part of compound 10 | 12.5 |
| 0.1 part of compound 11 | 12.5 |
| 0.05 part of compound 11 | 9.0 |
| 0.025 part of compound 11 | 7.5 |
| 0.1 part of compound 12 | 9 |
| 0.1 part of compound 13 | 10 |
| 0.1 part of compound 14 | 13 |

-continued

| Stabiliser | Time in minutes until the turning moment changes |
|---|---|
| none | 3 |

EXAMPLE 23

Examination of the oxidation behaviour of turbine oils and hydraulic oils (a) Accelerated "CIGRE" method (modified method IP 280)

A stream of oxygen of 4 liters per hour is passed through 25 g of oil at 150° C. during 4 hours. The oil contains as catalyst 20 mg of Fe (III) per kg of oil and 20 mg of Cu (II) per kg of oil. At the end of the test, the amount of the formed acid dissolved in the oil is determined.

(b) Oxidation in the rotating bomb: "ROBOT" according to ASTM D 2272/IP 229

The oil to be tested is placed, together with water and a copper coil as catalyst, into a glass vessel, and the glass vessel is transferred to a pressure vessel provided with a pressure registering device. After the pressure vessel has been flushed with oxygen and the pressure adjusted to 6.25 bars (90 psi), the vessel is axially rotated in a bath at constant temperature (150° C.). The time until there occurs a pressure loss of 1.7 bars (25 psi) is determined.

| Base oil: Solvent Neutralol, viscosity at 100° C. 10.6 c St ($mm^2$/sec.) | | | |
|---|---|---|---|
| Compound No. | Conc. % | Accelerated CIGRE acid number (mg of KCH/g) | ROBOT (ASTMD-2272) Time until loss of pressure in vessel is 1.7 bars |
| 8 | 0.5 | 0.44 | 116 |
| 10 | 0.5 | 0.26 | 459 |
| 18 | 0.5 | 0.22 | 322 |
| 11 | 0.5 | 0.85 | |
| Base oil: without additive | | 3.6 | 16 |

I claim:
1. 6-(2,4-di-tert.-octyl-phenoxy)-dibenz[c,e]-[1,2]oxaphosphorine.

* * * * *